(12) United States Patent
Magner et al.

(10) Patent No.: US 7,485,230 B2
(45) Date of Patent: Feb. 3, 2009

(54) INTEGRATED COGENERATION WASTEWATER SEWAGE AND WASTE POLAR FATS/ OILS/ GREASES/WAXES (FOG) WASTE TREATMENT METHOD AND FACILITY

(76) Inventors: Joseph A. Magner, 621 Mayfair Ave., South San Francisco, CA (US) 94080; Richard V. York, 5725 Dogwood Dr., Weed, CA (US) 96094-9504

( * ) Notice: Subject to any disclaimer, the term of this patent is extended or adjusted under 35 U.S.C. 154(b) by 63 days.

(21) Appl. No.: 11/683,877

(22) Filed: Mar. 8, 2007

(65) Prior Publication Data

US 2008/0203014 A1 Aug. 28, 2008

Related U.S. Application Data

(60) Provisional application No. 60/892,068, filed on Feb. 28, 2007.

(51) Int. Cl.
*C02F 3/28* (2006.01)
*C02F 11/04* (2006.01)
(52) U.S. Cl. .................. 210/603; 210/613; 210/180; 210/259; 210/916; 435/262.5
(58) Field of Classification Search .......... 210/603, 210/612, 613, 173, 175, 180, 252, 259, 922; 435/262, 262.5
See application file for complete search history.

(56) References Cited

U.S. PATENT DOCUMENTS

| 4,372,856 | A | | 2/1983 | Morrison |
| 4,559,142 | A | * | 12/1985 | Morper ......................... 210/607 |
| 4,721,569 | A | * | 1/1988 | Northrop ...................... 210/607 |
| 4,871,283 | A | | 10/1989 | Wright |
| 6,224,646 | B1 | | 5/2001 | Arato et al. |
| 6,464,875 | B1 | * | 10/2002 | Woodruff ...................... 210/603 |
| 6,692,642 | B2 | * | 2/2004 | Josse et al. ................... 210/605 |

(Continued)

FOREIGN PATENT DOCUMENTS

JP 2002-153897 * 5/2002

OTHER PUBLICATIONS

Chevron Energy Solutions Company, a Division of Chevron U.S.A. Inc.; "Cogeneration & Grease Receiving Station Project,—Report and Proposal"; Dated Feb. 3, 2005; pp. 17-20, and Attachment 1 pp. 2-5 of Detailed Scope of Work. [Available from the City of Millbrae, CA pursuant a Freedom of Information Request].

(Continued)

*Primary Examiner*—Fred Prince

(57) ABSTRACT

A system and method integrating treatment of waste, polar Fats/Oils/Greases (FOG) with conventional anaerobic wastewater treatment facilities for biologically fueling digestion of solids in, and steady state production of methane from treated wastewater streams that includes a slipstream loop circulating warmed, actively digesting sludge from the base to the head of the anaerobic wastewater treatment facility, a conditioning tank with input screened by a rock trap, actively digesting sludge pumped from the slipstream loop into the tank via the rock trap, before and after FOG wastes are pumped from a hauler tank via a hose connecting to the rock trap into the conditioning tank and mixed with actively digesting sludge in the tank to produce a feedstock slurry rich in volatile fatty acids for injection at a metered rate back into the actively digesting sludge slipstream loop for introduction at the head of the anaerobic wastewater treatment facility.

14 Claims, 2 Drawing Sheets

U.S. PATENT DOCUMENTS

| | | |
|---|---|---|
| 6,838,000 B2 * | 1/2005 | Braun .......................... 210/603 |
| 6,893,556 B2 * | 5/2005 | Yaegashi et al. ......... 210/167.29 |
| 2003/0094002 A1 | 5/2003 | Hibino et al. |
| 2005/0056588 A1 | 3/2005 | Petering |
| 2006/0004237 A1 * | 1/2006 | Appel et al. ................. 585/241 |
| 2006/0096163 A1 * | 5/2006 | Dickinson et al. ............. 44/552 |
| 2006/0175252 A1 | 8/2006 | Upendrakumar |
| 2006/0289356 A1 | 12/2006 | Burnett et al. |
| 2007/0095734 A1 * | 5/2007 | Lee ............................ 210/180 |
| 2007/0098625 A1 * | 5/2007 | Adams et al. ............... 423/484 |

OTHER PUBLICATIONS

Chevron Energy Solutions Company, a Division of Chevron U.S.A. Inc. and the City of Millbrae, CA; "Energy Services Contract"; Dated Apr. 27, 2005, Attachment D—Scope of Work pp. 2 & 3-5. [Available from the City of Millbrae, CA pursuant a Freedom of Information Request].

* cited by examiner

INTEGRATED COGENERATION WASTEWATER SEWAGE AND WASTE POLAR FATS/ OILS/ GREASES/WAXES (FOG) WASTE TREATMENT METHOD AND FACILITY

RELATED APPLICATIONS

This Application claims all benefits applicable under 35 U.S.C. §119(e) related to U.S. Provisional Patent Application Ser. No. 60/892,068 filed on behalf of the Applicants on Feb. 28, 2007 also entitled "INTEGRATED COGENERATION WASTEWATER SEWAGE AND WASTE POLAR FATS/OILS/GREASES/WAXES (FOG) WASTE TREATMENT METHOD AND FACILITY", which is incorporated herein by reference in its entirety.

BACKGROUND OF THE INVENTION

1. Field of the Invention

The invention relates to integrated digestible wastes (sewage and otherwise) and waste polar fats/oils/greases/waxes (FOG) treatment methods, systems and facilities including anaerobic digesters and steady-state generation of methane.

2. Description of the Prior Art

Excessive concentrations of FOG (fats, oils, waxes and greases) are a major problem in wastewater/sewage collection and treatment systems. There are two types of FOG. The first type, polar FOG originates from animals or vegetable (foods). Because of the prevalence of food service and processing enterprises in populated environs, polar FOG is responsible for a large percentage of sewer system failures and overflows. In particular, polar FOG, if not intercepted congeals on and sticks to piping and fixtures in wastewater systems, and, as well, to other debris flowing in the waste stream creating plugs and causing functional failures of the sewer system components.

The second type, non-polar FOG, is from petroleum or mineral origins, i.e., is petroleum-based oils, waxes, and greases. This type of FOG is typically detrimental to wastewater treatment systems/processes and, in particular, to the biologic phase of waste treatment process inhibiting (poisoning) microorganisms that breakdown or digest the wastes. Introduction of non-polar FOG into a sewage treatment system is generally prohibited by law and penalized when possible.

Publicly owned sewage treatment systems typically, by statutes, ordinances, and/or regulations, require food service and processing enterprises discharging waste in to public systems to have, and regularly maintain grease traps and interceptors to prevent introduction of generated polar FOG into treatment systems. Grease traps and interceptors are baffled tanks or basins that functionally rely on the immiscibility and the different densities of wastewater and FOG. Wastewater with FOG and other materials are input near the tank top and pools on one side of the baffle(s). The wastewater flows the beneath the baffles trapping less dense FOG floating, cooling and congealing on the water surface behind the baffle. The more dense and FOG'ed (coated) solid materials input with the wastewater settle to the tank bottom. Wastewater exits the tank near the top on the opposite side of the baffle(s) for the most part, sans low density FOG and other high-density materials. However, grease traps and interceptors have limited capacities. The accumulated, floating and congealed FOG and heavier coated materials settled on the tank bottom must be regularly removed, otherwise the trap/interceptors can plug up. Or more seriously, as the traps/interceptors approach capacity, input wastewater tends to entrain both FOG and other materials as it streams through the FOG/solids filled trap/interceptor tank inducing failures downstream in the sewer system.

Best management practices taught by publicly owned wastewater treatment operations mandate regular clean outs of both grease traps and interceptors preferably by professional FOG haulers and recyclers licensed for handling and properly disposing of 'BROWN' FOG, i.e., polar FOG contaminated with raw sewage and solids that typically collect in grease traps and interceptors. The simplest and probably most economical mode of cleaning out grease traps and interceptors is to isolate the trap/interceptor in the plumbing system, and then to pump or 'vacuum' the entire contents of the trap or interceptor tank/basin into a truck or trailer tank. Caked grease/fat is then steam or pressure-cleaned from the interior tank/basin walls with the wash accumulate being vacuumed into the truck or trailer tank. The so tanked 'BROWN' FOG evacuate from grease traps/interceptors is an unholy, difficult to handle, smelly, watery, sticky mess.

Properly disposing of such tanked 'BROWN' FOG evacuate is a problem precisely because it is contaminated, contains rocks, glass, tableware, both broken and not, bones and other items people thoughtlessly, or purposely toss/flush down drains at public and commercial establishments. Historically, such 'BROWN' FOG evacuate has been deemed 'toxic' and is required to be disposed of in landfills appropriately isolated from aquifers and surface drainages. Existing appropriate disposal sites are filling up, and new sites are difficult to find, and once found, economically expensive to establish and maintain. Finally, after a landfill site reaches capacity, its possible uses are limited far into the foreseeable future.

It is well recognized in wastewater management fields that 'BROWN' FOG also comprises a source of feedstock suitable for digestion, with the benefits of biogas production including methane for electrical power generation and heating. For example, the South Bayside System Authority (SBSA) located in Redwood City, Calif. has been accepting 'BROWN' FOG evacuate from 13 or so permitted haulers since the early 1990's at rates of 1500 to 3000 gallons per day, that after removal of indigestible solids (rocks, glass & tableware) produce approximately 20 cubic feet of digester gas (60% methane) per gallon of greases when introduced into a single mesophilic anaerobic digester. Problems experienced at the SBSA facility primarily relate to handling of the 'BROWN' FOG evacuate, and to spiking of biogas production with each cleaned 'BROWN' FOG evacuate loaded into the digester. The Wastewater Division of the City of Oxnard, Calif. (OWD) actually provides a municipal grease trap/interceptor cleanout service with personnel and vacuum trucks for local food servicing and processing enterprises. The collected 'BROWN' FOG evacuate is input via grease feed and horizontal chopper pumps to one of three 110 foot anaerobic digesters where mixing is enhanced using gas draft tubes. Again, the problems experienced at the OWD treatment plant, akin to those at SBSA, relate to material handling (clogs) and spiking biogas production when the 'BROWN' FOG evacuate is offloaded to the digester.

SUMMARY OF THE INVENTION

An invented integrated cogeneration digestible wastes, and polar fats/oils/greases/waxes (FOG) waste treatment method, system and facility is described that includes a warmed sludge, slipstream loop incorporating circulation pumps, a hot water heat exchanger and a conventional anaerobic digester system continuously circulating actively digesting sludge from the bottom or base of the digester system, and then back to the top or head end of the digester system at a rate for precluding solid settlement accumulation as a warm flowable slurry source. The actively digesting sludge is warmed by the heat exchanger at least to a temperature sufficient to soften and/or liquefy polar FOG. The warmed, actively digesting sludge is pumped from the slipstream loop through a rock trap and a delivery/input line (i) for aiding transport of delivered 'BROWN' and/or 'YELLOW' FOG wastes offloaded via a rock trap from a tank hauler via a hose connected to the rock trap and the input line, and (ii) for partially filling a closed, vented, receiving/conditioning holding tank with offloaded FOG and actively digesting sludge. The offloaded FOG waste and the actively digesting sludge in the closed, vented, receiving/conditioning holding tank, are continuously mixed by a bottom-top, recirculation, chopper pump to pre-treat the FOG wastes, liquefying, hydrolyzing and decreasing solids particle size to allow acidogens in the sludge to pre-digest such wastes producing volatile fatty acids, some biogas and a highly bioreactive, flowable, feedstock slurry. The highly bioreactive, flowable, feedstock slurry is then injected back into the warmed sludge slipstream loop at a controlled (metered) rate, whereupon the mixture is introduced, together with raw sewage or other digestible wastes, into the top or head end of an anaerobic digester system for solids digestion and steady-state methane production.

Advantages of the integrated system relate to (i) a positive net energy gain from increased steady-state methane production suited for electricity generation using micro-turbines, or for combustion as a thermal energy source and/or for storage, and to (iii) significantly reduced solids volume output of both the treated sewage/digestible wastes and FOG wastes.

Novel aspects of the invented integrated system relate to the pre-treatment circulation of 'BROWN' and 'YELLOW' FOG waste and the actively digesting sludge in the storage/reaction holding tank for partial digestion of the FOG, generating volatile fatty acids that suppress expression of sludge methane producing methagens in the reaction/holding tank while simultaneously converting the sticky, gooey FOG and digesting sludge into a miscible, highly bioreactive, flowable, feedstock slurry ideally suited for driving anaerobic digestion of raw sewage and other digestible wastes.

Other novel aspects of the invented integrated generation system relate to the maintenance of ratios of the offloaded FOG waste volume to actively digesting sludge input into the receiving/conditioning holding tank.

An important feature of the invented integrated cogeneration system is that the actively digesting sludge is input into the delivery input line immediately upstream from a rock trap sieving offloading tanked 'BROWN' FOG accumulate just before and just after the FOG waste is offloaded from a tank truck. This process assures the delivery/input line is always warm and pre-coated with actively digesting sludge before the sticky FOG is offloaded, and is subsequently scoured by the actively digesting sludge after the sticky FOG is offloaded removing any adhering greases/oils/fats/waxes and particulate in the line thereby essentially eliminating possibilities of a clog-up during subsequent offloads.

Still other novel aspects of the invented integrated cogeneration system relate to automating offloading processes, automating filling, circulation, and metering flowable the miscible, highly bioreactive, feedstock slurry from the receiving/conditioning holding tank, and automating temperature maintenance processes within the actively digesting sludge slipstream loop.

Still other aspects of the invented integrated cogeneration system affords servo control for optimizing both digestion processes in the digesters and steady-state methane production for electrical power generation inherent in the capacity to meter introduction of a highly bioreactive, flowable feedstock slurry from the reaction/holding tank into the continuously circulating warm, actively digesting sludge slipstream loop for introduction with sewage and/or other digestible wastes into anaerobic digester systems.

It also should be appreciated that while the invented integrated cogeneration system is presented in context of anaerobic primary and secondary digesters, an AGMM system, the invented processes and systems are equally applicable to any sewage treatment systems having an anaerobic digester in schemes that include aerobic and other types of digesters, e.g. AGTM and AGMT systems.

DESCRIPTION OF PREFERRED AND EXEMPLARY EMBODIMENTS

DETAILED DESCRIPTION OF EXISTING AND PREFERRED EMBODIMENTS

Figure 1:
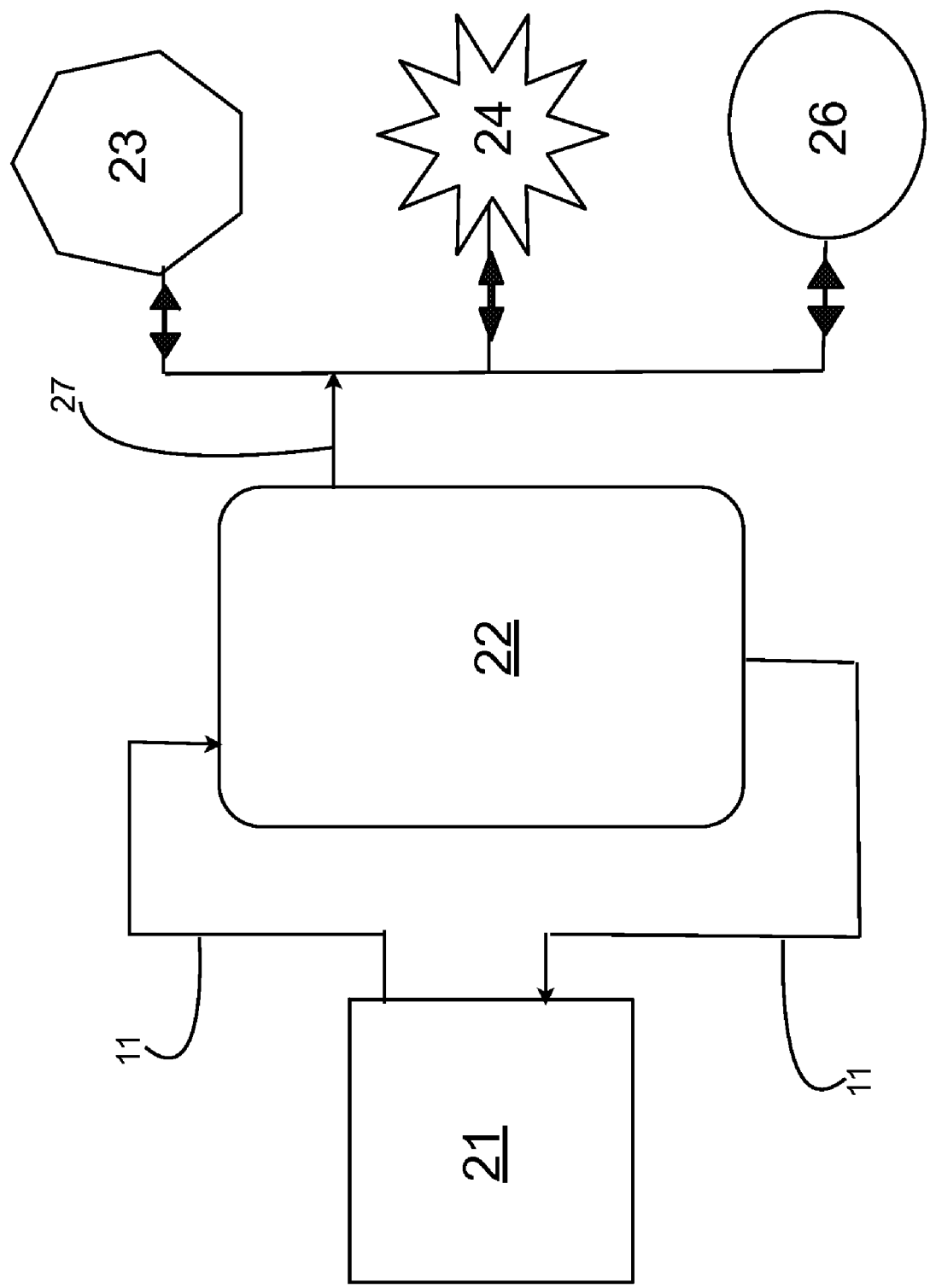
FIG. 1 is a block diagram showing the FOG receiving/pre-treatment station, the digestible wastes processing system, and output utilization of produced methane.

Looking at FIG. 1 the invented integrated cogeneration system for treating raw sewage, and polar fats/oils/greases/waxes (FOG) wastes includes a FOG receiving and pre-treatment station 21 receiving actively digesting sludge circulating in a slipstream loop 11 from the base or bottom of a digestible wastes treatment facility 22, and outputting a highly bioreactive, flowable, feedstock slurry mixed with actively digesting sludge circulating in the slipstream loop 11 to the top or head/input end of the wastes treatment facility 22. Produced methane gas is either used to generated electrical power 23, combusted to produce thermal energy 24, or stored 26 for future use.

The wastes treatment facility 22 is located in Millbrae, Calif. and is an Acid/Gas Mesophilic acid phase—Mesophilic gas phase (AGMM) system where a primary anaerobic digester receives raw sewage, and pours over to a secondary anaerobic digester. The overall objective of the integration was to increase steady-state methane production 27 at the facility at no cost to rate payers for purpose of driving a micro-turbine electrical power generator 23 for increased electrical power generation at the facility, and to reduce solids volumes from the digesters, while providing a fee generating service capable of receiving and processing so called 'BROWN' FOG evacuate from grease traps/inceptors tanked on tucks and/or trailers by licensed FOG haulers servicing food service and processing enterprises in the San Francisco Bay region and surrounding areas.

In January, 2007 construction of the Millbrae facility was essentially completed, and shakedown operations and processes testing and experimentation with constructed system began. Those operations, tests and experimentations are ongoing during preparation of this application. The purpose of the shakedown operations, and testing and experimentation is to determine optimal operating conditions for the unique parameters at the Millbrae facility. In particular, every sewage treatment facility has its unique populations of digesting flora that depend on system operating parameters and the diverse nutrients, chemistries, temperatures, and other biological factors in the incoming wastewater and waste streams being treated.

Figure 2:
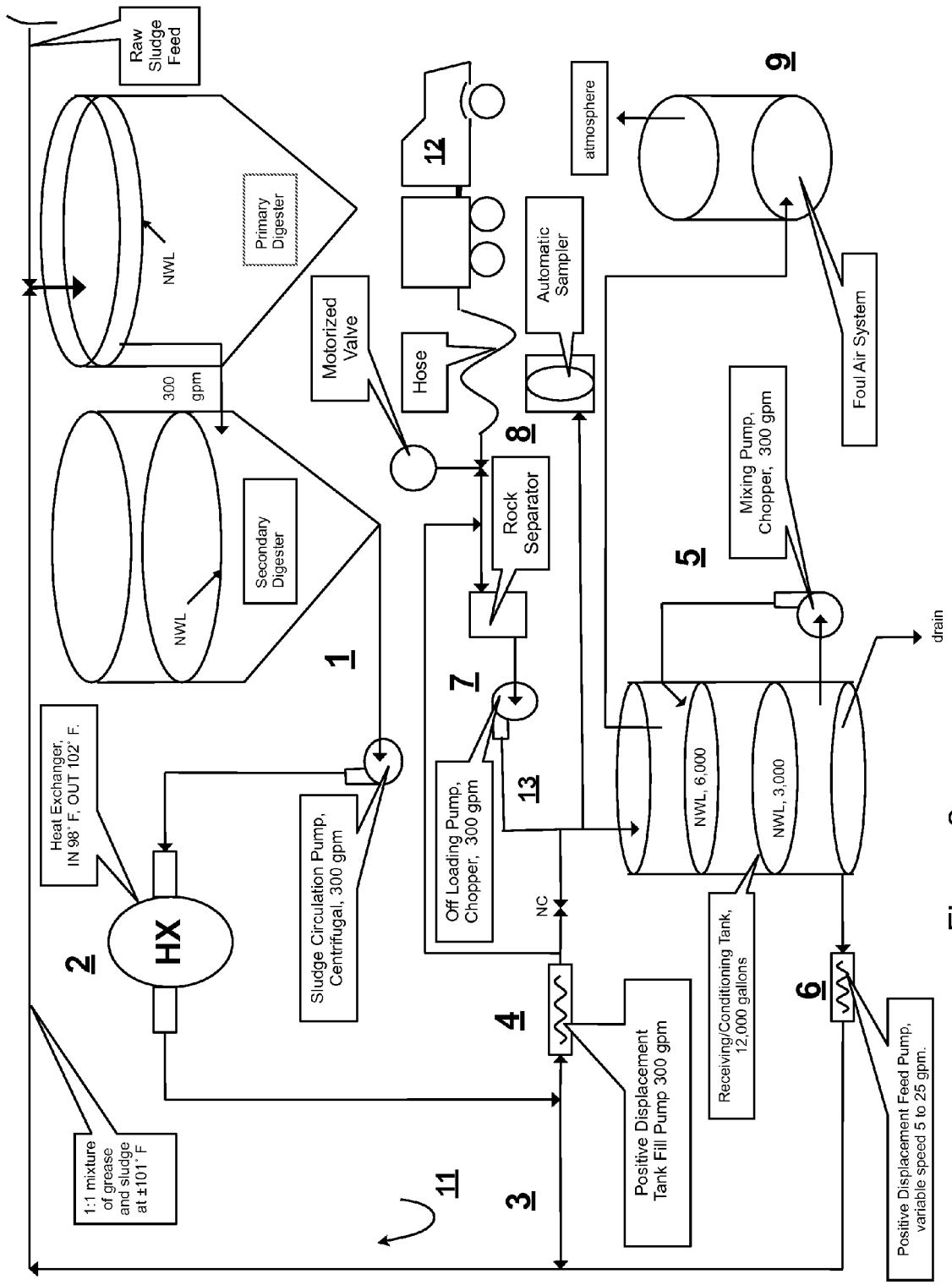
FIG. 2 presents a labeled diagram of the invented integrated cogeneration system for treating raw sewage, and polar fats/oils/greases/waxes (FOG) wastes designed by, and constructed under the direction the Applicants at the Water Pollution Control Plant for the City of Millbrae, Calif. located at the 400 Last Millbrae Avenue at the east end of the on-ramp to Interstate 101.

The applicants contend that their invented process and systems for receiving, processing and introducing 'BROWN' FOG evacuate from grease traps/inceptors or even collected 'YELLOW' FOG, i.e. polar fats/oils/greases/waxes not contaminated with raw sewage, for cogeneration of methane and associated electricity can be integrated into any wastewater treatment facility having an anaerobic digester in its treatment scheme including but not necessarily limited to Acid/Gas Thermophilic acid phase—Mesophilic gas phase (AGTM) systems; and Acid/Gas Mesophilic acid phase—Thermophilic gas phase (AGMT) systems As indicated in greater detail in the labeled flow diagram of FIG. 2, the constructed system includes a warmed sludge slipstream loop indicated by the arrow 11 that flows from the bottom or base of a secondary anaerobic digester, includes a 300 gpm sludge circulation pump 1, a hot water heat exchanger 2, and that then returns back 3 to the top or head of a primary digester. As indicated, actively digesting sludge is withdrawn from the base of the secondary digester is warmed to temperatures of up to 104° F. (40° C.) and is circulated in the loop at rates up to 300 gpm. A positive displacement pump 4 also having a capacity of up to 300 gpm, on demand, pumps the warmed, actively digesting sludge from the slipstream loop through a rock separator 8, an offloading chopper pump (with a similar pumping capacity of up to 300 gpm) through a delivery/input piping 13 to a closed, vented, receiving/conditioning, holding tank 5. A bottom-top recirculation chopper pump circulates from bottom-to-top, contents pumped into the receiving/conditioning holding tank 5 for pre-treating and conditioning the FOG wastes, liquefying, hydrolyzing and decreasing solids particle size and inducing the acidogens in the sludge to pre-digest such wastes to produce volatile fatty acids, some biogas and a miscible, highly bioreactive, flowable FOG/sludge feedstock slurry. Biogas produced in the receiving/conditioning holding tank 5 is vented from the holding tank and is scrubbed 9 to remove possible offending odorants and thereafter preferably burned for producing energy.

A second positive displacement pump 6 injects the bioreactive, miscible, FOG/sludge, flowable feedstock slurry pumped from near the base of the holding tank back into the warmed sludge slipstream loop 11 at a meterable rate from 1 gpm up to 25 gpm, whereupon it circulates in the slipstream piping mixing with the actively digesting sludge and then is introduced with the sludge along with raw wastewater sewage and/or other digestible wastes into the head or input end of anaerobic digesters for reducing solids output and greatly increasing steady-state methane production from the digesters.

The volume ratio of warmed, circulating actively digesting sludge to the volume of the flowable and miscible FOG/sludge feedstock slurry injected from the holding tank 5 back into the slipstream loop should be maintained such that the acidogens and volatile acids in the slurry are buffered minimizing inhibition of the methagens carried by the circulating, actively digesting sludge in the slipstream loop.

In more detail as indicated in FIG. 1, polar FOG wastes, 'BROWN' and/or 'YELLOW', are pumped from a tank hauler 12 operated by a licensed commercial hauler, via a hose connecting to a rock trap 8 by an offloading pump 7 into the receiving/conditioning holding tank 5. In particular, the hauler pulls onto an offloading drain basin bib. A motion sensor will activate a camera for documenting the offloading event, and, if dark, turn on lights to illuminate the area. The commercial hauler starts the process by swiping an authorizing and identifying magnetic ID card for capturing an account number, driver name, truck serial number, before allowing access to a hose box, and then initiates recording of receipt manifests for evidencing delivery/receipt of the load.

When continuity is sensed between the hose connection and tanker truck (via a ground clamp), a traffic gate is lowered to remind the hauler that the tanker is connected to hose and to open a manual block valve. Once the manual block valve is opened, the offloading sequence is enabled.

In particular, the first positive displacement tank fill pump 4 will initially discharge a sufficient quantity of the warmed, actively digesting sludge into the rock separator 8 to warm and coat the rock separator 8, the offloading chopper pump 7 and the input line piping 13 to the closed, vented, receiving/conditioning holding tank 5. However, the FOG receiving system is pre-programmed such that the positive displacement tank fill pump 4 automatically maintains a minimum volume ($V_1$) in the holding tank, i.e. at a level in the holding tank 5 higher than the second positive displacement metering pump 6 outlet. Once temperature in the input line 13 is achieved, a motorized block valve opens and the chopper pump activates to offload the FOG from the tank hauler 12. The FOG evacuate is periodically sampled by an automatic sampler as it is offloaded.

To preclude any possibility of back filling the tank hauler 12 with liquids circulating in the system facilities, an interlock on the motorized valves shuts off the sludge circulation pump 1, both positive displacement pumps 4 & 6 and the bottom-top recirculation chopper pump 5 recirculating and mixing the contents in the holding tank 5. The tank truck hauler 12 initiates a wash cycle to assure a complete offloading of the FOG using a pressure steam or hot water wash system (not shown) either associated with the tank hauler 12 or made available at the drain basin bib. In the event of a spill, piping (not shown) connects the offloading pump 7 for pumping spilled FOG wastes and associated liquids from the drain basin bib.

A sensor in the holding tank 5 senses a starting level in the tank upon initiation of the offloading by the chopper pump 7, and an ending level upon completion of the offload, i.e., when the tank level ceases to rise over an appropriate time interval. A delivered volume ($V_H$) is then calculated and printed on the manifest delivery receipt for the hauler and recorded in separate manifest received record maintained by the treatment facility. The motorized offloading block valve then begins to close and interlocks shuts down the offloading chopper pump 7. Once the motorized block valve is fully closed, the sludge circulation pump 1, the positive displacement pumps 4 & 6, and the bottom-top recirculation chopper pump all resume pumping. The positive displacement pumps 4 immediately starts pumping warmed, actively digesting sludge from the slipstream loop into the receiving/conditioning tank for flushing and scouring the rock trap and offloading input piping 13 and then adds a specific volume ($V_2$) of the warmed, actively digesting sludge to the holding tank 5 to establish a specified sludge to offloaded FOG volume ratio.

To explain, there will be an existing volume of the already fully, or not so fully conditioned flowable, bioreactive FOG feedstock slurry, or just actively digesting sludge in the holding tank 5 at a particular (lower) temperature than that of the warmed actively digesting sludge circulating in the slipstream loop. The offloaded raw FOG further cools the holding tank contents, While the acidogens are quite hardy and resilient to temperature swing, there are optimum conditions that relate to temperature, mixing achieved by the bottom-top recirculation mixing chopper pump, the acidogens in the newly input actively digesting sludge and the nature of the FOG offloaded. The Applicants suggest volume ratios of the flowable miscible, bioreactive FOG/feedstock slurry with actively digesting sludge already in the holding tank ($V_1$): the FOG volume ($V_H$) offloaded into the holding tank: the subsequent volume ($V_2$) of warmed, actively digesting sludge thereafter added to the holding tank be set at 1:1:1 as a starting point for testing and experimentation to determine optimum conditions for pre-treating/conditioning the FOG and actively digesting sludge in the holding tank. The objective of the testing and experimentation is to create a highly bioreactive, flowable, feedstock slurry in the holding tank that is optimized for continuous anaerobic digestion together with raw treatable/digestible wastes, including but not limited to sewage, in the waste processing/treatment systems of the particular facility for reducing solids output and increasing steady-state methane production.

Periodically, warmed, actively digesting sludge from the slipstream loop should be pumped into, almost filling the holding tank 5 and circulated by the bottom/top mixing pump in the tank 5 for a set time-period to scour and flush the holding tank. Sewage system operators should also appreciate that maintaining a set minimum volume ($V_1$) or level of liquid in holding tank in the manner described, automatically fluctuates the volume of introduced actively digesting sludge in the tank over time. That is, when the holding tank level drops to a predetermined low level, the tank fill pump 4 comes on to fill the holding tank to the predetermined minimum volume ($V_1$). In this way, the meterable feed pump 6 injecting the holding tank contents back into the circulating slipstream loop can be run continually, and the FOG receiving station system components may be flushed clean by introduced actively digesting sludge between offloads of FOG delivered by tank haulers to the system.

The advantages of the invented integrated system of a FOG receiving and pre-treatment station with a two-phase mesophilic acid phase and mesophilic gas phase wastewater treatment facility is that it is a simple system to operate and maintain manually, and is easily amenable to automation and automatic operation using programmable logic controllers (PLC).

Skilled sewage system operators should also appreciate that the receiving/conditioning holding tank essentially comprises an acid phase digester ideally suited for digesting 'BROWN' and 'YELLOW' polar FOG wastes using actively digesting sludge for creating a highly bioreactive, flowable, feedstock slurry that can be stored, further concentrated, and even tanked and transported to other locations as fuel for other anaerobic waste digestion systems, driving digestion of wastes other than sewage, to reduce the output volume of digested solids and increase steady-state methane production (energy generation) by such systems. In fact, initial measurements of stored, fully conditioned, highly bioreactive, flowable, feedstock slurry taken from the receiving/conditioning holding tank at the Water Pollution Control Plant in Millbrae, Calif. indicate that the stored bioreactive feedstock slurry does not produce or outgas any gases, in particular methane, meaning that all methagens in the actively digesting sludge mixed and conditioned with the FOG in the holding tank were eradicated by the low pH fatty acids produced by acidogens in the sludge in an acid phase digestion of the FOG wastes occurring in the holding tank.

The invented system also avoids problems of emulsified grease at the input or head end of the waste digestion cycles in a treatment plants. In particular, FOG from grease traps and interceptors transported in tank haulers from collection points to the treatment plants will always have a component of emulsified FOG in the accompanying wastewater due to the nature of washing and cleaning procedures of grease traps/interceptors by the waste haulers and the sloshing and vibration experienced during tank transport. Precluding emulsified grease from entering wastewater plant treatment processes is a highly recommended, promoted and regulated best management practice for sewage and waste treatment facilities.

Finally, skilled sewage system operators should also appreciate that the invented system allows for continuous processing of digestible wastes and FOG, in that the receiving/conditioning holding tank reservoirs the acid phase digestion of the FOG by the acidogens in actively digesting sludge, the low pH fatty acids precluding propagation of the methagens in the holding tank. The resultant slurry of digested FOG and sludge is a highly bioreactive, flowable, feedstock that can be metered over time into an actively digesting sludge stream and introduced at the input or head end of any anaerobic waste treatment cycle, not just an isolated a digester, along with other raw digestible wastes for continuous, as opposed to batch digestion, thus avoiding sharp (possibly explosive) methane production peaks. In short, preliminary results at the Millbrae Water Pollution Control Plant demonstrate an increase in steady-state methane production of more than 100%, and a significant reduction (50%) in digested solids volumes over and under that, respectively, which existed before integration of the FOG receiving system into the facility.

We claim:

1. An integrated wastes, and polar fats/oils/greases/waxes (FOG) waste treatment method, the steps comprising:
   a) circulating actively digesting sludge in a slipstream loop at a rate for precluding solid settlement accumulation as a flowable slurry from a base and back to a head of an anaerobic wastewater digester system;
   b) warming the circulating actively digesting sludge to a temperature at least sufficient to soften polar FOG for a desired sewage treatment temperature range;
   c) initially pumping a set volume ($V_1$) of the warmed, circulating, actively digesting sludge from the slipstream loop though a rock trap and a delivery/input line piping into, for partially filling a closed, vented receiving/conditioning, holding tank;
   d) connecting a hauler tank containing a volume ($V_H$) of FOG wastes via an offloading hose to the rock trap;
   e) pumping the entire FOG waste volume ($V_H$) from the hauler tank though the rock trap and the delivery/input piping into the closed, vented, receiving/conditioning, holding tank;
   f) pumping a second volume ($V_2$) of the warmed circulating actively digesting sludge from the slipstream loop via the rock trap and delivery/input piping into the closed, vented, receiving/conditioning holding tank where ($V_1$):($V_H$):($V_2$) have a pre-selected relationship and ($V_1$)+($V_H$)+($V_2$) is less than the volume of the receiving/conditioning holding tank;
   g) mixing the warmed, circulating actively digesting sludge with the FOG wastes in the receiving/conditioning holding tank for liquefying, hydrolyzing and decreasing solids particle size of the FOG wastes and allowing acidogens in the actively digesting sludge to pre-digest such wastes, producing volatile fatty acids, some biogas, and from the FOG wastes and actively digesting sludge, a highly bioreactive, flowable, feedstock slurry;

h) injecting at a metered rate the highly bioreactive, flowable, feedstock slurry from the receiving/conditioning holding tank back into slipstream loop circulating the warmed, actively digesting sludge slurry; and i) introducing the highly bioreactive, flowable, feedstock slurry with the actively digesting sludge slurry in the slipstream loop together with raw digestible wastes at the head of the anaerobic digester system for solids digestion and steady-state methane production.

2. A pre-treating method for polar fats/oils/greases/waxes (FOG) wastes comprising the steps of:

a) circulating actively digesting sludge from an anaerobic wastewater digester system in a slipstream loop as a flowable slurry at a rate for precluding solid settlement accumulation;

b) warming the circulating actively digesting sludge to a temperature at least sufficient to soften polar FOG for a desired sewage treatment temperature range;

c) initially pumping a set volume ($V_1$) of the warmed, circulating, actively digesting sludge from the slipstream loop though a rock trap and a delivery/input line piping into, for partially filling a closed, vented receiving/conditioning, holding tank;

d) connecting a hauler tank containing a volume ($V_H$) of FOG wastes via an offloading hose to the rock trap;

e) pumping the entire FOG waste volume ($V_H$) from the hauler tank though the rock trap and the delivery/input piping into the closed, vented, receiving/conditioning, holding tank;

f) pumping a second volume ($V_2$) of the warmed circulating actively digesting sludge from the slipstream loop via the rock trap and delivery/input piping into the closed, vented, receiving/conditioning holding tank where ($V_1$):($V_H$):($V_2$) have a pre-selected relationship and ($V_1$)+($V_H$)+($V_2$) is less than the volume of the receiving/conditioning holding tank;

g) mixing the warmed circulating actively digesting sludge with the FOG wastes in the receiving/conditioning holding tank for liquefying, hydrolyzing and decreasing solids particle size of the FOG wastes and allowing acidogens in the actively digesting sludge to pre-digest such wastes, producing volatile fatty acids, some biogas, and from the FOG wastes and actively digesting sludge, a highly bioreactive, flowable, feedstock slurry suitable for fueling solids digestion, and steady-state methane production in anaerobic waste digester systems.

3. The method of claim 1 or 2 further including a step of maintaining a volume of contents in the closed, vented, receiving/conditioning holding tank at volume ($V_1$) between offloads of FOG wastes from hauler tanks with warmed, actively digesting sludge pumped from the slipstream loop as the highly bioreactive, flowable, feedstock slurry is pumped from the receiving/conditioning holding tank.

4. The method of claim 1 or 2 wherein the closed, vented, receiving/conditioning holding tank contains a residual volume ($V_R$) of the highly bioreactive, flowable, feedstock slurry and a start volume ($V_S$) of warmed circulating actively digesting sludge pumped from the slipstream loop into the receiving/conditioning holding tank is adjusted downward to a specific volume at least equal to the volume of the rock trap and the delivery/input line piping, where ($V_S$)+($V_R$)=($V_1$).

5. The method of claim 1 or 2 further including the step of generating electrical power with any produced methane.

6. The method of claim 1 or 2 further including a step combusting a portion of any produced methane for providing thermal energy.

7. The method of claim 1 or 2 further including a step of storing a portion of any produced methane.

8. A integrated digestible wastes, and polar fats/oils/greases/waxes (FOG) waste treatment system comprising, in combination:

a) a digestible wastes treatment system having an anaerobic digester;

b) a slipstream loop for circulating actively digesting sludge at a rate for precluding solid settlement accumulation from a base of the anaerobic digester back to an input head of the digestible wastes treatment system as a flowable slurry;

c) a sludge pump for circulating the actively digesting sludge in the slipstream loop from the anaerobic digester;

d) a heat exchanger heating the actively digesting sludge received in the circulating slip stream-loop from the sludge pump for warming the actively digesting sludge to a temperature at least sufficient to soften polar FOG for a desired sewage treatment temperature range;

e) a rock separator coupled by a delivery/input piping to a closed, vented, receiving/conditioning, holding tank f) an offloading hose connectable between the rock separator and a tank hauler transporting FOG wastes;

g) an offloading chopper pump for pumping an entire volume ($V_H$) of FOG waste from the tank hauler via the offloading hose through the rock separator via the delivery/input piping into the closed, vented, receiving/conditioning, holding tank;

h) a positive tank fill pump for pumping initially, a set volume ($V_1$) of warmed, circulating actively digesting sludge from the slipstream loop though the rock separator and delivery/input line into, to partially fill the closed, vented, receiving/conditioning, holding tank before offloading of FOG wastes from a hauler tank, and then pumping a second volume ($V_2$) of warmed, circulating actively digesting sludge from the slipstream loop after offloading of the FOG wastes from the tank hauler though the rock separator and delivery/input line to the closed receiving/conditioning, holding tank, and thereafter, pumping actively digesting sludge from the slipstream loop into the holding tank for maintaining the volume of contents in the holding tank at the set volume ($V_1$), where ($V_1$):($V_H$):($V_2$) have a pre-selected relationship and ($V_1$)+($V_H$)+($V_2$) is less than the volume of the receiving/conditioning holding tank;

i) a bottom-top, recirculation chopper pump connected for circulating material from the bottom to the top of the receiving/conditioning, holding tank for mixing received warmed, actively digesting sludge and FOG wastes in the holding tank for liquefying, hydrolyzing and decreasing solids particle size of the FOG wastes and for allowing acidogens in the actively digesting sludge to pre-digest such wastes, producing volatile fatty acids, some biogas and, from the FOG wastes and actively digesting sludge, a highly bioreactive, flowable, feedstock slurry;

j) a positive displacement pump connected for injecting at a metered rate the highly bioreactive, flowable, feedstock slurry from the receiving/conditioning holding tank back into the slipstream loop to circulate and mix with the warmed, actively digesting sludge slurry for input at the head of the of the digestible wastes treatment system, with raw digestible wastes, into the digestible wastes treatment system for solids digestion and steady-state methane production.

9. A polar fats/oils/greases/waxes (FOG) waste treatment system comprising, in combination:

a) a slurry source of flowable actively digesting sludge;

b) a sludge pump for continuously circulating the actively digesting sludge in a slipstream loop at a rate for precluding solid settlement accumulation;

c) a heat exchanger heating the actively digesting sludge in the slip stream loop received from the sludge pump warming it to a temperature at least sufficient to soften polar FOG for a desired sewage treatment temperature range;

d) a rock trap coupled by delivery/input piping to a closed, vented, receiving/conditioning, holding tank e) an offloading hose connectable between the rock trap and a tank hauler transporting FOG wastes;

f) an offloading chopper pump for pumping an entire volume ($V_H$) of FOG waste from the tank hauler via the offloading hose through the rock trap via the delivery/input piping into the closed, vented receiving/conditioning, holding tank;

g) a positive tank fill pump for pumping initially a set volume ($V_1$) of warmed circulating actively digesting sludge from the slipstream loop though the rock trap and delivery/input piping into, to partially fill the closed, vented, receiving/conditioning, holding tank before the offloading of FOG wastes from a hauler tank, and then pumping a second volume ($V_2$) of warmed circulating actively digesting sludge from the slipstream loop after offloading the FOG wastes from the tank hauler though the rock trap and delivery/input line to the closed receiving/conditioning, holding tank, and thereafter, pumping actively digesting sludge from the slipstream loop into the holding tank for maintaining the volume of contents in the holding tank at the set volume ($V_1$), where ($V_1$): ($V_H$):($V_2$) have a pre-selected relationship and ($V_1$)+($V_H$)+($V_2$) is less than the volume of the receiving/conditioning holding tank;

h) a bottom-top, recirculation chopper pump connected for circulating material from the bottom to the top of the receiving/conditioning, holding tank for mixing the warmed actively digesting sludge with the FOG waste in the receiving/conditioning holding tank for liquefying, hydrolyzing and decreasing solids particle size of the FOG wastes and for allowing acidogens in the actively digesting sludge to pre-digest such wastes, producing volatile fatty acids, some biogas, and, from the FOG wastes and actively digesting sludge, a highly bioreactive, flowable, feedstock slurry suitable for fueling solids digestion, and steady-state methane production in anaerobic wastes digester systems.

10. The system of claim 8 or 9 wherein the closed, vented, receiving/conditioning holding tank contains a residual volume ($V_R$) of the highly bioreactive, flowable, feedstock slurry and a start volume ($V_S$) of warmed circulating actively digesting sludge from the slipstream loop is pumped into the receiving/conditioning holding tank at least equal to the volume of the rock trap and the delivery/input piping, where ($V_R$)+($V_S$)=($V_1$).

11. The system of claim 8 or 9 and further including means for generating electrical energy from the methane produced by the waste digester systems.

12. The system of claim 8 or 9 and further including means for controllably combusting the produced methane for providing useful thermal energy.

13. The system of claim 8 or 9 and further including means for storing the produced methane for future use.

14. The waste treatment methods or systems of claims 1 or 2, or, claims 8 or 9 respectively, further including deodorizing the produced biogas with a scrubber receiving the biogases from a vent from the closed, vented, receiving/conditioning holding tank.

* * * * *